US009220758B2

(12) United States Patent
Mehta et al.

(10) Patent No.: US 9,220,758 B2
(45) Date of Patent: Dec. 29, 2015

(54) CALCITONIN PRODUCTS AND THERAPIES FOR TREATING INFLAMMATORY OR DEGENERATIVE DISEASES

(71) Applicant: UGP Therapeutics, Inc., Chicago, IL (US)

(72) Inventors: Nozer M. Mehta, Randolph, NJ (US); James P. Gilligan, Union, NJ (US)

(73) Assignee: UGP Therapeutics, Inc., Chicago, IL (US)

( * ) Notice: Subject to any disclaimer, the term of this patent is extended or adjusted under 35 U.S.C. 154(b) by 0 days.

(21) Appl. No.: 14/046,501

(22) Filed: Oct. 4, 2013

(65) Prior Publication Data

US 2014/0249085 A1    Sep. 4, 2014

Related U.S. Application Data

(63) Continuation of application No. 13/238,801, filed on Sep. 21, 2011, now abandoned.

(60) Provisional application No. 61/385,078, filed on Sep. 21, 2010.

(51) Int. Cl.
| | | |
|---|---|---|
| *A61K 38/23* | (2006.01) | |
| *A61K 31/65* | (2006.01) | |
| *C07K 14/585* | (2006.01) | |
| *A61P 19/02* | (2006.01) | |
| *A61K 45/06* | (2006.01) | |
| *A61K 31/381* | (2006.01) | |
| *A61K 31/404* | (2006.01) | |
| *A61K 31/415* | (2006.01) | |
| *A61K 31/573* | (2006.01) | |
| *A61K 38/17* | (2006.01) | |

(52) U.S. Cl.
CPC .............. *A61K 38/23* (2013.01); *A61K 31/381* (2013.01); *A61K 31/404* (2013.01); *A61K 31/415* (2013.01); *A61K 31/573* (2013.01); *A61K 31/65* (2013.01); *A61K 38/17* (2013.01); *A61K 45/06* (2013.01)

(58) Field of Classification Search
CPC ..... A61K 38/23; A61K 45/06; A61K 31/381; A61K 31/404; A61K 31/415; A61K 31/573; A61K 31/65; A61K 38/17; A61K 2300/00
See application file for complete search history.

(56) References Cited

U.S. PATENT DOCUMENTS

| | | |
|---|---|---|
| 2006/0194722 A1 | 8/2006 | Azria |
| 2008/0160025 A1 | 7/2008 | MacIntyre et al. |
| 2008/0226737 A1 | 9/2008 | Azria |
| 2009/0035315 A1 | 2/2009 | Christgau |
| 2010/0015196 A1 | 1/2010 | Kimbie et al. |
| 2010/0158905 A1 | 6/2010 | Pearlman |

FOREIGN PATENT DOCUMENTS

| | | |
|---|---|---|
| WO | WO-0004924 | 2/2000 |
| WO | WO-0047203 | 8/2000 |
| WO | WO-0113957 | 3/2001 |
| WO | WO-2004098571 | 11/2004 |
| WO | WO-2004101017 | 11/2004 |
| WO | WO-2005000266 | 1/2005 |
| WO | WO-2005000949 | 5/2005 |
| WO | WO-2006103455 | 10/2006 |

OTHER PUBLICATIONS

Brandt et al, Effects of Doxycycline on Progression of Osteoarthritis Results of a Randomized, Placebo-Controlled, Double-Blind Trial, Arthritis & Rheumatism, 2005, 52, pp. 2015-2025.*
Nganvongpanit et al, The effect of doxycycline on canine hip osteoarthritis: design of a 6-months clinical trial, J. Vet. Sci., 2009 10, pp. 239-247, published online on Sep. 7, 2009.*
Aida et al., "Calcitonin inhibits production of immunoglobulins, rheumatoid factor and interleukin-1 by mononuclear cells from patients with rheumatoid arthritis", Annals of Rheumatic Disease, 53(4):247-249 (1994).
Aida, "Effects of eel calcitonin on rheumatoid arthritis", Annals of the Rheumatic Diseases, 50(3):202-203 (1991).
Becker et al., "Clinical review 167: Procalcitonin and the calcitonin gene family of peptides in inflammation, infection, and sepsis: a journey from calcitonin back to its precursors", Journal of Clinical Endocrinology and Metabolism, 89(4):1512-1525 (2004).
Conway et al., "Inhibition of cartilage and bone destruction in adjuvant arthritis in the rat by a matrix metalloproteinase inhibitor", Journal of Experimental Medicine, 182(2):449-457 (1995).
Cooper et al., "Rheumatoid arthritis, corticosteroid therapy and hip fracture", Annals of the Rheumatic Diseases, 54(1):49-52 (1995).

(Continued)

*Primary Examiner* — Julie Ha
*Assistant Examiner* — Li Ni Komatsu
(74) *Attorney, Agent, or Firm* — Ropes & Gray LLP; Melissa Rones; Brian M. Gummow

(57) ABSTRACT

Calcitonin products and therapies for treating inflammatory or degenerative diseases are disclosed herein. The pharmaceutical compositions disclosed herein include a first therapeutic agent that is calcitonin, in free or salt form; a second therapeutic agent selected from the group consisting of a protease inhibitor, an antibiotic, a non-steroidal anti-inflammatory agent, a cyclooxygenase-2 (COX-2) inhibitor and a steroidal anti-inflammatory agent other than glucocorticoid; and a pharmaceutically acceptable excipient, carrier or diluent. The methods disclosed herein for treating inflammatory or degenerative diseases in a subject include administering a therapeutically effective amount of calcitonin, in free or salt form, to the subject; and co-administering, as part of a combination therapy, a therapeutically effective amount of a second therapeutic agent selected from the group consisting of a protease inhibitor, an antibiotic, a non-steroidal anti-inflammatory agent, a COX-2 inhibitor and a steroidal anti-inflammatory agent other than glucocorticoid to the subject.

13 Claims, 8 Drawing Sheets

(56) References Cited

OTHER PUBLICATIONS

Goldstein et al., "Chronic glucocorticoid therapy-induced osteoporosis in patients with obstructive lung disease", Chest, 116(6):1733-1749 (1999).

PCT International Search Report for International Appln. No. PCT/US11/52612, mailed Feb. 8, 2012.

Badurski et al., "Therapeutic use of Calcitonin in Concomitant Diseases of the Joints and Stomach II. Clinical Assesment of Calcitonin Effect on Chronic Peptide Ulcer in Patients with Rheumatoid Arthritis and Degenerative Joint Disease", Biosciences Information Service, Philadelphia, PA (8 pages) (1987), Summary only.

Badurski et al., "Therapeutic User of Calcitonin in Concomitant Diseases of the Joints and Stomach", Philadelphia, PA (1986), Summary only.

Beers et al., "The Merck Manual of Diagnosis and Therapy," eds. published by Merck Research Laboratories, 17th ed., pp. 469-473 (1999).

Bobalik et al., "Effects of salmon calcitonin and combination drug therapy on rat adjuvant arthritis," Agents and Actions, 4(5):364-369 (1974).

Consoli et al., "Calcitonin in the osteoporosis of rheumatic disease. Preliminary physiopathologic and clinical aspects and evaluation";, La Clinica Terapeutica, 118(1):37-47 (1996), Summary only.

Gospodinoff et al., "Calcitonin in the treatment of coxarthrosis", La Clinica Terapeutica, 110(2):129-133 (1984), Summary only.

Ljunghall et al., "Synthetic human calcitonin in postmenopausal osteoporosis: a placebo-controlled, double-blind study", Calcified Tissue International, 49(1):17-19 (1991).

Townsend et al., "Glucocorticoid use in rheumatoid arthritis: benefits, mechanisms, and risks," Clinical and Experimental Rheumatology, 22:(5 Suppl 35):S77-S82 (2004).

Waldmann, "Immunotherapy: past, present and future," Nature Medicine, 9(3):269-77 (2003).

\* cited by examiner

CALCITONIN PRODUCTS AND THERAPIES FOR TREATING INFLAMMATORY OR DEGENERATIVE DISEASES

RELATED APPLICATIONS

This application is a continuation of U.S. patent application Ser. No. 13/238,801, filed on Sep. 21, 2011, which claims the benefit of and priority to U.S. Provisional Patent Application No. 61/385,078, filed on Sep. 21, 2010, which are hereby incorporated herein by reference in their entireties for the teachings therein.

FIELD

The present disclosure relates to combination therapy for the treatment of inflammatory or degenerative diseases, and particularly to the use of calcitonin in combination with at least one other active agent for treating such inflammatory or degenerative diseases, and to therapeutic products that include both calcitonin and at least one other active agent.

BACKGROUND

Inflammatory or degenerative diseases, including diseases of the joints, e.g. osteoarthritis (OA), rheumatoid arthritis (RA) or juvenile rheumatoid arthritis (JRA), and including inflammation that results from autoimmune response, e.g. lupus, ankylosing spondylitis (AS) or multiple sclerosis (MS), can lead to substantial loss of mobility due to pain and joint destruction. Cartilage that covers and cushions bone within joints may become degraded over time thus undesirably permitting direct contact of two bones that can limit motion of one bone relative to the other and/or cause damage to one by the other during motion of the joint. Subchondral bone just beneath the cartilage may also degrade. However, compounds helpful in preventing bone loss will not necessarily prevent cartilage degradation. Cartilage may be degraded by proteases present in synovial fluid that covers the cartilage surface or from white blood cells that infiltrate the joint space.

Diseases such as osteoarthritis are multimodal in nature, rendering it difficult for any single therapeutic agent to effectively treat all of the symptoms of the disease. Inflammatory or degenerative diseases of the joints have been treated with a variety of therapeutic agents, including a range of non-steroidal anti-inflammatory drugs (NSAIDs) that possess both analgesic and anti-inflammatory properties, but without ideal clinical success in many instances. The NSAIDs in particular provide symptomatic relief but fail to adequately protect the joints from further disease progression. Monotherapy to date has failed to adequately provide both a chondroprotective effect while also providing improved mobility and reduced pain, all of which are attributes for disease-modifying osteoarthritis drugs (DMOADs). Additionally, some therapeutic agents have shown undesirable side effects at the dosages required for therapeutic efficacy.

SUMMARY

Calcitonin products and therapies for treating inflammatory or degenerative diseases in a subject are disclosed herein. Treatment may be of a human or a non-human subject. In an embodiment, a therapy of the present disclosure permits a combination of therapeutic agents to be effective at lower dosages than would be necessary if the therapeutic agents were used singly. In an embodiment, the use of lower dosages results in a lower risk of side effects that are sometimes associated with monotherapies.

According to aspects illustrated herein, there is provided a method for treating a degenerative or an inflammatory disease that includes administering calcitonin, in free or salt form, to a subject in need of such treatment; and administering, as part of a combination therapy, a second therapeutic agent for treatment of an inflammatory or degenerative disease, the second therapeutic agent not being a glucocorticoid. In an embodiment, at least additive effectiveness is achieved by the combination relative to administering only the second therapeutic agent in the absence of the calcitonin.

According to aspects illustrated herein, there is provided a method for treating a degenerative or an inflammatory disease in a subject that includes administering a therapeutically effective amount of calcitonin, in free or salt form, to the subject; and co-administering, as part of a combination therapy, a therapeutically effective amount of a COX-2 inhibitor. In an embodiment, at least additive effectiveness is achieved by the combination relative to administering only the COX-2 inhibitor in the absence of the calcitonin.

According to aspects illustrated herein, there is provided a method for treating a degenerative or an inflammatory disease in a subject that includes administering a therapeutically effective amount of calcitonin, in free or salt form, to the subject; and co-administering, as part of a combination therapy, a therapeutically effective amount of a matrix metalloproteinase inhibitor. In an embodiment, at least additive effectiveness is achieved by the combination relative to administering only the matrix metalloproteinase inhibitor in the absence of the calcitonin.

According to aspects illustrated herein, there is provided a method for treating a degenerative or an inflammatory disease in a subject that includes administering a therapeutically effective amount of calcitonin, in free or salt form, to the subject; and co-administering, as part of a combination therapy, a therapeutically effective amount of an interleukin antagonist. In an embodiment, at least additive effectiveness is achieved by the combination relative to administering only the interleukin antagonists in the absence of the calcitonin.

According to aspects illustrated herein, there is provided a method for treating a degenerative or an inflammatory disease in a subject that includes administering a therapeutically effective amount of calcitonin, in free or salt form, to the subject; and co-administering, as part of a combination therapy, a therapeutically effective amount of a tetracycline antibiotic. In an embodiment, at least additive effectiveness is achieved by the combination relative to administering only the tetracycline antibiotic in the absence of the calcitonin.

According to aspects illustrated herein, there is provided a method for treating a degenerative or an inflammatory disease that includes administering a calcitonin, in free or salt form, to a subject in need of such treatment; and further administering, as part of a combination therapy, a second therapeutic agent selected from the group consisting of a protease inhibitor, an antibiotic, a non-steroidal anti-inflammatory agent, a COX-2 inhibitor and a steroidal anti-inflammatory agent other than a glucocorticoid.

According to aspects illustrated herein, there is provided a method for reducing the effective dosage (such as the approved dosage) of a therapeutic agent for treatment of an inflammatory or a degenerative disease that includes administering the therapeutic agent and calcitonin, in free or salt form, as part of a combination therapy, to a subject in need of treatment for the inflammatory or degenerative disease.

According to aspects illustrated herein, there is provided a method for treating an inflammatory or a degenerative disease that includes administering to a subject in need of such treatment, as part of a combination therapy, (A) calcitonin, in free or salt form, and (B) a second therapeutic agent for treatment of an inflammatory or degenerative disease, wherein the second therapeutic agent is administered at a dosage no higher than 90% of the normal dosage for the second therapeutic agent when administered alone.

According to aspects illustrated herein, there is provided a method for treating a degenerative or an inflammatory disease that includes administering calcitonin, in free or salt form, to a subject in need of such treatment; and administering, as part of a combination therapy, an additional agent selected from the group consisting of a protease inhibitor, an antibiotic, a non-steroidal anti-inflammatory agent, a COX-2 inhibitor and a steroidal anti-inflammatory agent other than glucocorticoid, wherein at least additive therapeutic effectiveness is achieved by the combination relative to administering only the additional agent in the absence of calcitonin.

According to aspects illustrated herein, there is provided a method for treating a degenerative or an inflammatory disease that includes administering a therapeutically effective amount of calcitonin, in free or salt form, to a subject in need of such treatment; and administering, as part of a combination therapy, a therapeutically effective amount of a second therapeutic agent selected from the group consisting of Galardin, Doxycycline and BB-94.

According to aspects illustrated herein, there is provided a pharmaceutical composition that includes a first therapeutic agent that is calcitonin, in free or salt form; a second therapeutic agent, wherein the second therapeutic agent is not a glucocorticoid; and a pharmaceutically acceptable excipient, carrier or diluent.

According to aspects illustrated herein, there is provided a pharmaceutical composition that includes a first therapeutic agent that is calcitonin, in free or salt form; a second therapeutic agent selected from the group consisting of a protease inhibitor, an antibiotic, a non-steroidal anti-inflammatory agent, a COX-2 inhibitor and a steroidal anti-inflammatory agent other than glucocorticoid; and a pharmaceutically acceptable excipient, carrier or diluent.

According to aspects illustrated herein, there is provided a pharmaceutical composition that includes a first therapeutic agent that is calcitonin, in free or salt form; a second therapeutic agent selected from the group consisting of Galardin, Doxycycline and BB-94; and a pharmaceutically acceptable excipient, carrier or diluent.

According to aspects illustrated herein, there is provided a kit for the treatment of a degenerative or an inflammatory disease that includes a first container having therein a first therapeutic agent that is calcitonin, in free or salt form; and a second container having therein a second therapeutic agent, wherein the second therapeutic agent is not a glucocorticoid.

According to aspects illustrated herein, there is provided a kit for the treatment of a degenerative or an inflammatory disease that includes a first container having therein a first therapeutic agent that is calcitonin, in free or salt form; and a second container having therein a second therapeutic agent selected from the group consisting of a protease inhibitor, an antibiotic, a non-steroidal anti-inflammatory agent, a COX-2 inhibitor and a steroidal anti-inflammatory agent other than glucocorticoid.

According to aspects illustrated herein, there is provided a kit for the treatment of a degenerative or an inflammatory disease that includes a unit dosage of a first therapeutic agent that is calcitonin, in free or salt form; and a unit dosage of a second therapeutic agent selected from the group consisting of a protease inhibitor, an antibiotic, a non-steroidal anti-inflammatory agent, a COX-2 inhibitor and a steroidal anti-inflammatory agent other than glucocorticoid.

According to aspects illustrated herein, there is provided a kit for the treatment of a degenerative or an inflammatory disease that includes a first container having therein a first therapeutic agent that is calcitonin, in free or salt form; and a second container having therein a second therapeutic agent selected from the group consisting of Galardin, Doxycycline and BB-94.

BRIEF DESCRIPTION OF THE DRAWINGS

The presently disclosed embodiments will be further explained with reference to the attached drawings.

Figure 1:
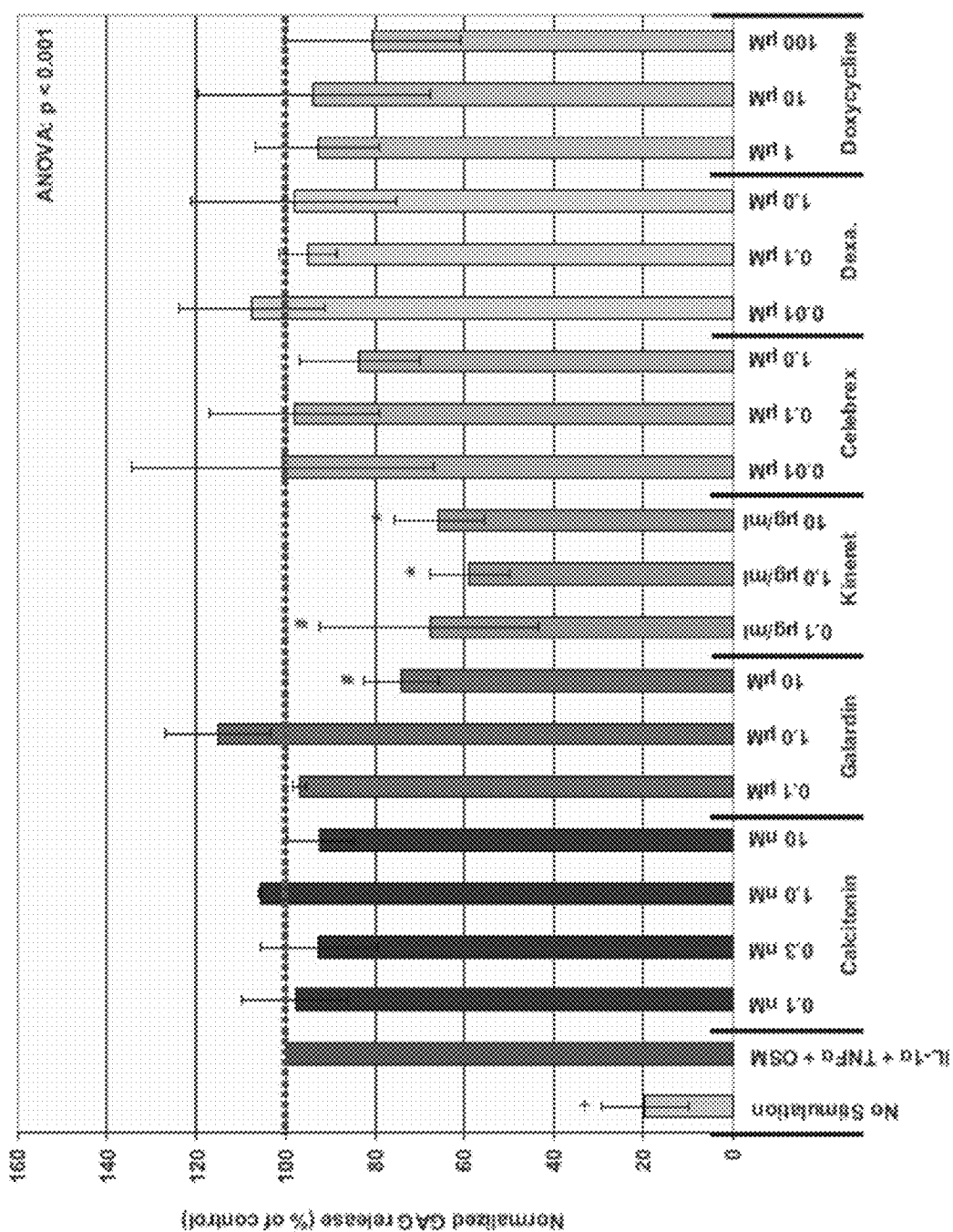
FIG. 1 is a bar chart showing the effect of treatment on proteoglycan release from stimulated bovine articular cartilage explants, measured as GAGs. The normalized GAG release in the culture medium during the three week culture is shown. The dotted line represents the GAG release from the control condition to which all conditions are compared.

While the above-identified figures set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

As used herein, the term "additive effect" and "additive effectiveness" refers to an effect in which two or more therapeutic active agents used in combination produce a total effect essentially the same as the sum of their individual effects.

As used herein, the term "synergistic effect" refers to an effect arising between two or more therapeutic agents used in combination that produces an effect greater than the sum of their individual effects.

As used herein, the term "therapeutically effective amount" refers to the amount/dose of an active therapeutic agent or a pharmaceutical dosage form that is sufficient to produce an effective response (i.e., a biological or medical response of a tissue, system, animal or human sought by a researcher, veterinarian, medical doctor or other clinician) upon administration to a subject. The "therapeutically effective amount" will vary depending on inter alia the disease and its severity, and the age, weight, physical condition and responsiveness of the patient to be treated.

As used herein, "co-administering" and "co-administration" refers to the administration of calcitonin and at least one additional therapeutic active agent together. In some embodiments, one or more therapeutic active agents may be formulated for oral administration (including buccal or sublingual) in solid or liquid form, for parenteral (including subcutaneous, intramuscular, intravenous, intraperitoneal, intra-arterial, or intradermal) route, for vaginal, nasal, topical (including buccal, sublingual or transdermal), or rectal administration. In some embodiments, one or more therapeutic active agents may be administered orally utilizing oral dosage forms such as those disclosed in U.S. Pat. No. 6,086,918 (Stern et al), or as disclosed in pending U.S. patent application Ser. No. 12/128,210 (Stern et al, published as US 2009/0317462). In other embodiments, one or more therapeutic active agents may be administered nasally using formulations such as those set forth in pending U.S. patent application Ser. No. 12/732,081 (Stern, published as US 2010/0256060). All of the therapeutic active agents used in any of the therapies discussed herein may be formulated in pharmaceutical compositions which also include one or more of the other therapeutic active agents. Alternatively, the therapeutic active agents may each be administered separately but sufficiently simultaneous in time so that a patient eventually has elevated blood levels or otherwise enjoys the benefits of each of the active ingredients (or strategies) simultaneously. In an embodiment, one or more active ingredients are to be formulated in a single pharmaceutical composition. In an embodiment, a kit is provided which includes at least two unit dosages, generally provided in separate sealed containers, wherein the contents of at least one container differs, in whole or in part, from the contents of at least one other container with respect to active ingredients contained therein. Combination therapies discussed herein also include use of one therapeutic active agent (of the combination) in the manufacture of a medicament for the treatment of the disease in question where the treatment further includes another active ingredient of the combination in accordance with the disclosure.

Except when otherwise noted or where apparent from context, dosages herein refer to weight of active compounds unaffected by pharmaceutical excipients, diluents, carriers or other ingredients, although such additional ingredients are desirably included. Any dosage form (e.g. solid dosage forms: including powders, granules, tablets, capsules, and suppositories; injections; nasal sprays; patches; depot injections or the like) commonly used in the pharmaceutical industry may be used to administer one or more active agents discussed herein, and the terms "excipient," "diluent," or "carrier" include such nonactive ingredients as are typically included, together with active ingredients in such dosage forms in the industry. For example, typical capsules, pills, enteric coatings, solid or liquid diluents or excipients, flavorants, preservatives, or the like may be included.

The present disclosure relates to combination therapies for the treatment of an inflammatory or a degenerative disease, and particularly to the use of calcitonin in combination with at least one other active agent for treating such inflammatory or degenerative diseases, and to therapeutic products that include both calcitonin and at least one other active agent. The combination therapies of the present disclosure are used for the treatment of inflammatory or degenerative diseases such as inflammatory diseases of the joints and degenerative diseases of the joints. Such diseases include, but are not limited to, osteoarthritis (OA), rheumatoid arthritis (RA), juvenile rheumatoid arthritis (JRA), lupus, ankylosing spondylitis (AS) and multiple sclerosis (MS). OA is a degenerative joint disease and a major cause of disability in the elderly. The hallmark of OA is the progressive destruction of articular cartilage (in addition to changes in subchondral bone, synovial membrane, and other joint tissues). RA is an autoimmune disease that involves pain and inflammation of the joints and surrounding tissues. It can also lead to loss of bone in the affected joints. Both OA and RA are multimodal in nature.

Evidence suggests a direct anabolic effect of calcitonin on articular chondrocytes, resulting in increased proteoglycan synthesis. The anticatabolic effects of calcitonin may involve induction of cAMP, resulting in attenuation of matrix metalloproteases (MMP)-mediated cartilage degradation. This inhibition of metalloproteases has been supported by measuring a decrease in C-terminal crosslinked telopeptide type II collagen (CTX-II) levels which are a surrogate marker for Type II collagen, a major constituent of articular cartilage.

In accordance with the present disclosure, calcitonin is used as part of a combination therapy with at least one other therapeutic agent effective to treat an inflammatory or a degenerative disease of the joints. In an embodiment, such a combination therapy has additive effectiveness, relative to use of calcitonin alone or relative to use of the other therapeutic agent alone. In an embodiment, such a combination therapy has synergistic effectiveness, relative to use of calcitonin alone or relative to use of the other therapeutic agent alone. This evidence of additive or synergistic results relates to effectiveness on parameters expected to be markers of effectiveness in reducing processes implicated in inflammatory or degenerative diseases. Because these processes are multimodal, a combination therapy may be useful by providing additive or synergistic effect on any one of the involved processes.

In addition to enhanced effectiveness, in an embodiment a combination therapy of the present disclosure may, because of the additive or synergistic effects, reduce the dosage required for therapeutic effectiveness of the second (non-calcitonin) therapeutic agent, thus reducing the likelihood of side effects that have diminished the desirability of these agents for some patients.

In an embodiment, a combination therapy of the present disclosure includes an effective dose of calcitonin and an effective does of at least one COX-2 inhibitor, where the effective dose of the COX-2 inhibitor in the combination therapy is less than an effective dose of a COX-2 inhibitor administered in a regular (i.e., non-combination) therapy protocol. Examples of COX-2 inhibitors include, but are not limited to, valdecoxib, celecoxib, etoricoxib and rofecoxib.

In an embodiment, a combination therapy of the present disclosure includes an effective dose of calcitonin and an effective does of at least one MMP inhibitor, where the effective dose of the MMP inhibitor in the combination therapy is less than an effective dose of a MMP inhibitor administered in a regular (i.e., non-combination) therapy protocol. Examples of MMP inhibitors include, but are not limited to, galardin, BB-94, and solimastat.

In an embodiment, a combination therapy of the present disclosure includes an effective dose of calcitonin and an effective does of at least one interleukin antagonist, where the effective dose of the interleukin antagonist in the combination therapy is less than an effective dose of an interleukin antagonist administered in a regular (i.e., non-combination) therapy protocol. Examples of an interleukin antagonist include anakinra (Kineret®).

In an embodiment, a combination therapy of the present disclosure includes an effective dose of calcitonin and an effective does of at least one antibiotic, where the effective dose of the antibiotic in the combination therapy is less than an effective dose of an antibiotic administered in a regular (i.e., non-combination) therapy protocol. Examples of antibiotics include, but are not limited to, doxycycline, minocycline, oxytetracycline, enrofloxacin, ceftiofur, salinomycin, and tetracycline.

In an embodiment, a combination therapy of the present disclosure includes an effective dose of calcitonin and an effective does of at least one NSAID, where the effective dose of the antibiotic in the combination therapy is less than an effective dose of an antibiotic administered in a regular (i.e., non-combination) therapy protocol. Examples of NSAID's include, but are not limited to, aspirin, ibuprofen, and naproxen In some embodiments, the non-calcitonin second therapeutic agent used in the combination therapy is used at a dosage no higher than 90 percent, no higher than 80 percent, no higher than 70 percent, of its recommended or effective dosage when used alone.

All of the therapeutic agents used in any of the combination therapies disclosed herein may be formulated in pharmaceutical compositions which also include one or more of the other therapeutic agents. Alternatively, the therapeutic agents may each be administered separately but sufficiently simultaneous in time so that a subject eventually has elevated blood levels or otherwise enjoys the benefits of each of the therapeutic agents simultaneously. In some embodiments of the present disclosure, for example, one or more therapeutic agents are to be formulated in a single pharmaceutical composition. Combination therapies discussed herein also include use of one therapeutic agent of the combination in the manufacture of a medicament for the treatment (or prevention) of the disease in question where the treatment or prevention further includes another therapeutic agents of the combination. While at least two active therapeutic agents are required in the combination therapies of the present disclosure, more than two of the therapeutic agents discussed herein (e.g., three or more such agents) are also contemplated and are within the scope of the present disclosure.

In an embodiment of the present disclosure, a kit is provided which includes at least two separate containers, wherein the contents of at least one container differs, in whole or in part, from the contents of at least one other container with respect to active therapeutic agents contained therein. Two or more different containers are used in the combination therapies of the present disclosure. In an embodiment, the present disclosure relates to a kit for the treatment of a degenerative or an inflammatory disease that includes a unit dosage form of a first therapeutic agent that is calcitonin, in free or salt form; and a unit dosage form of a second therapeutic agent, wherein the second therapeutic agent is not a glucocorticoid. Such a kit would normally (although not necessarily) include instructions for use. The kit may include a plurality of the unit dosage forms.

The Calcitonin

The calcitonin of the present disclosure may be any natural calcitonin, or any truncate and/or modification thereof that retains calcitonin's antiresorptive properties. The calcitonins used according to the present disclosure also include variants, fragments and/or derivatives of a calcitonin peptide. The calcitonin may be in free or salt form. Calcitonin has been characterized from many animal sources. Many types, both natural and synthetic, are known, including but not limited to human calcitonin, salmon calcitonin, eel calcitonin or an analog thereof (elcatonin). Except where otherwise stated or apparent from context, the term "calcitonin" as used herein is a generic term covering any and all calcitonins, natural or synthetic, including the above-noted truncates, and regardless of whether in free or salt form.

In an embodiment, salmon calcitonin is used in accordance with the present disclosure for a number of reasons. Salmon Calcitonin (sCT) is a naturally occurring amidated peptide hormone composed of 32 amino acids which binds to osteoclasts and inhibits bone resorption. Calcitonins from many species are effective in humans, but salmon calcitonin is most widely used. Salmon calcitonin is highly potent in humans because of its high affinity for the human calcitonin receptor and its slow rate of clearance. Thus, salmon calcitonin provides a number of advantages over even human calcitonin, even when used as a pharmaceutical agent for human patients. Among the advantages provided by utilizing salmon calcitonin instead of human calcitonin are increased potency, analgesia and increased half-life. Also, lower dosages are necessary than with human calcitonin. There is substantial non-homology between salmon and human calcitonin, with only 50% identity in the amino acid sequences of the two calcitonins Notwithstanding the foregoing preference for salmon calcitonin, other calcitonins may be used in accordance with the present disclosure.

In an embodiment, when salmon calcitonin is chosen as the calcitonin for a combination therapy of the present disclosure and is delivered orally as described above, concentration levels are between about 100 micrograms (μg) to about 1000 μg of salmon calcitonin per dosage form. In an embodiment, when salmon calcitonin is chosen as the calcitonin for a combination therapy of the present disclosure and is delivered orally as described above, concentration levels are between about 100 μg to about 400 μg of salmon calcitonin per dosage form. In an embodiment, when salmon calcitonin is chosen as the calcitonin for a combination therapy of the present disclosure and is delivered orally as described above, concentration levels are between about 150 μg to about 300 μg of salmon calcitonin per dosage form.

The calcitonin may be delivered in any conventional manner commonly utilized in the pharmaceutical industry. In an embodiment, the calcitonin is administered nasally in accordance with the teachings of Stern, U.S. Pat. RE 40,812. Nasal calcitonin products are available, e.g. FORTICAL® (available from Upsher-Smith). Such nasal calcitonin formulations may be modified to add a second therapeutic agent of the combination therapies discussed herein. In another embodiment, the calcitonin is delivered orally in accordance with the teachings of Stern et al, U.S. Pat. No. 6,086,918; or pending U.S. patent application Ser. No. 12/128,210 (Stern et al, published as US 2009/0317462). Such oral calcitonin formulations may be modified to add a second therapeutic agent of the combination therapies discussed herein. In some embodiments, the calcitonin and at least one additional therapeutic agent are combined in single pharmaceutical compositions. In some embodiments, the calcitonin and at least one additional therapeutic agent may be provided in unit dosage forms, and will generally be provided in one or more sealed containers and may be provided as part of a kit. Such a kit would normally (although not necessarily) include instructions for use. The kit may include a plurality of the unit dosage forms.

The Additional Agent of the Combination Therapy

The additional therapeutic agent of the present disclosure, which is used as part of a combination therapy with calcitonin, may be any therapeutic agent that is individually effective in the treatment of one or more inflammatory or degenerative diseases. These diseases include but are not limited to osteoarthritis (OA), rheumatoid arthritis (RA), juvenile rheumatoid arthritis (JRA), lupus, ankylosing spondylitis (AS) and multiple sclerosis (MS). Classes of such agents include, but are not limited to, antibiotics, steroidal anti-inflammatory agents, non-steroidal anti-inflammatory agents, COX-2 inhibitors, and protease inhibitors, especially MMP inhibitors that inhibit degradation of Type-II collagen and aggrecanase inhibitors. Examples of such agents for use in a combination therapy of the present disclosure include, but are not limited to, minocycline, doxycycline, oxytetracycline, enrofloxacin, ceftiofur, salinomycin, tetracycline, BB-94 (available from Tocris Bioscience as BATIMASTAT®), solimastat, Galardin (available from U.S. Biological as LLOMASTAT®), anakinra (available from Biovitrum as KINERET®), valdecoxib, celecoxib (available from Pfizer as CELEBREX®), etoricoxib, rofecoxib, aspirin, ibuprofen and naproxen (available from Bayer as ALEVE®).

In an embodiment, the additional therapeutic agent is administered at dosages reported to be effective for the therapeutic agent when administered alone. With respect to commercial products, the therapeutic agent may be administered at dosages recommended by the labeling/packaging of the product. However, it is believed that calcitonin may lower the effective dosage of the additional the therapeutic agent. In some embodiments, the additional the therapeutic agent is administered at a dosage no higher than 90 percent of the normal dosage, no higher than 80 percent of normal dosage, or in some embodiments, no higher than 70 percent of normal dosage. By reducing effective dosage of the additional the therapeutic agent, undesirable side effects associated with long term use of such agents as, for example, steroids, NSAIDs or COX-2 inhibitors, may be reduced.

The examples of combination therapies described in the following Examples, which are set forth to aid in the understanding of the disclosure, should not be construed to limit in any way the scope of the disclosure as defined in the claims which follow thereafter. The following examples are put forth so as to provide those of ordinary skill in the art with a complete disclosure and description of how to make and use the described embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

In an embodiment, the Examples below were carried out to identify whether the combination of salmon calcitonin and other active agents can produce additive or synergistic effects in reducing collagen degradation in a bovine in vitro collagen matrix model. Studies were designed to identify synergistic effects of salmon Calcitonin (sCT) with reference to treatments for osteoarthritis using the bovine cartilage explant model in which degradation is induced by a cocktail of three cytokines Matrix degradation was quantified by measuring proteoglycan release, collagen release and MMP activity. The pro-inflammatory molecule PGE2 was also measured. The studies consisted of two phases:

Phase 1: the highest ineffective dose of calcitonin and reference compounds (Galardin, Kineret® (anakinra), Celebrex® (celecoxib), Dexamethasone, BB-94 and Doxycycline) were determined in a bovine explant model for articular cartilage degradation.

Phase 2: the effect of calcitonin in combination with each of the reference compounds, in their highest ineffective dose, was studied to determine their synergistic effects in blocking cartilage destruction.

The studies were designed to identify classes of compounds that work synergistically to decrease parameters associated with the development and progression of OA and/or RA. These studies provide convincing demonstration of significant trends for critical parameters known to be involved in the etiology and pathogenesis of OA and RA.

EXAMPLES

Example 1

In this experiment, three or four concentrations of each compound were tested to find the highest ineffective dose, i.e., the concentration in which each compound has no or only a very small effect on cartilage degradation.

Full thickness cartilage was obtained from the metacarpophalangeal joints of approximately 6 months old calves (from a local slaughterhouse). Cartilage punches (4 mm) were taken from the cartilage and placed in culture dishes with culture medium (DMEM+FCS, penicillin, streptomycin and ascorbic acid). Cartilage explants were weighed and explants between about 5 and about 15 mg were divided into a 96-well culture plate with 1 explant per well and 200 µL culture medium. Cartilage degradation was induced by addition of TNFα, IL-1α, and OSM at 10 ng/mL each to the culture medium. Test agents were then added at different concentrations. During three weeks of culture, the culture medium and the test compounds were refreshed once weekly. In addition fresh calcitonin was added twice weekly to the cartilage explants. Culture medium and cartilage explants were stored at −20° C. until analysis. Each culture condition was cultured in four-fold and the entire experiment was performed on cartilage from three different paws. The different culture conditions are listed below in Table 1.

TABLE 1

| Culture Condition number | 10 ng/ml TNFa 10 ng/ml IL-1a 10 ng/ml OSM | Compound name | Compound concentration |
|---|---|---|---|
| 1 | % | % | % |
| 2 | + | — | — |
| 3 | + | Calcitonin | 10 nM |
| 4 | + | Calcitonin | 1 nM |
| 5 | + | Calcitonin | 0.3 nM |
| 6 | + | Calcitonin | 0.1 nM |
| 7 | + | Galardin | 10 μM |
| 8 | + | Galardin | 1 μM |
| 9 | + | Galardin | 0.1 μM |
| 10 | + | Kineret ® (anakinra) | 10 μg/ml |
| 11 | + | Kineret ® (anakinra) | 1 μg/ml |
| 12 | + | Kineret ® (anakinra) | 0.1 μg/ml |
| 13 | + | Celebrex ® (celecoxib) | 1 μM |
| 14 | + | Celebrex ® (celecoxib) | 0.1 μM |
| 15 | + | Celebrex ® (celecoxib) | 0.01 μM |
| 16 | + | Dexamethasone | 1 μM |
| 17 | + | Dexamethasone | 0.1 μM |
| 18 | + | Dexamethasone | 0.01 μM |
| 19 | + | Doxycycline | 100 μM |
| 20 | + | Doxycycline | 10 μM |
| 21 | + | Doxycycline | 1 μM |

Outcome parameters included (i) CTX-II in the culture medium as a measure of collagen degradation, (ii) GAG in the culture medium and cartilage explant as a measure of proteoglycan degradation, (iii) prostaglandin E2 (PGE2) measured by ELISA in the culture medium as a measure of inflammation, and (iv) general MMP activity in the culture medium. Not all outcome parameters were determined for each of the culture conditions.

Collagen Release:

Collagen release was measured as CTX-II release per mg cartilage. Collagen was measured in the pooled medium using the CTXII ELISA assay (Pre-clinical Cartilaps®, Nordic Bioscience). Stimulation with the combination of interleukin-1a (IL-1a), TNFα and oncostatin M (OSM) resulted in an upregulation of the CTX-II release from 14 to 135 ng/mg cartilage.

Proteoglycan Release:

The proteoglycan release is measured as GAG release per mg cartilage. Proteoglycan (GAG) content was determined in the pooled medium and explants using the Blyscan® colorimetric assay (Biocolor, Belfast, UK). This value is normalized against the control condition of each donor to correct for donor variation. The basal release of unstimulated cartilage is 36% (p<0.05) when the stimulated (IL-1a, TNFα and OSM) control is set to 100%.

PGE2 Release:

The prostaglandin E2 release was measured as PGE2 release per mg cartilage. PGE2 was determined in the pooled medium using a PGE2 ELISA from R&D Systems. This value was normalized against the control condition of each donor to correct for donor variation. The basal release of unstimulated cartilage is 11% (p<0.0 1) when the stimulated (IL-1a, TNFα and OSM) control is set to 100%.

MMP Activity:

The MMP activity was measured as MMP activity per mg cartilage. General MMP activity was determined in the pooled medium using the fluorogenic substrate TNO21 1-F. Stimulation with the combination of IL-1a, TNFα and OSM resulted in an upregulation of the MMP activity from 1 to 23 ng/mg cartilage.

Figure 2:
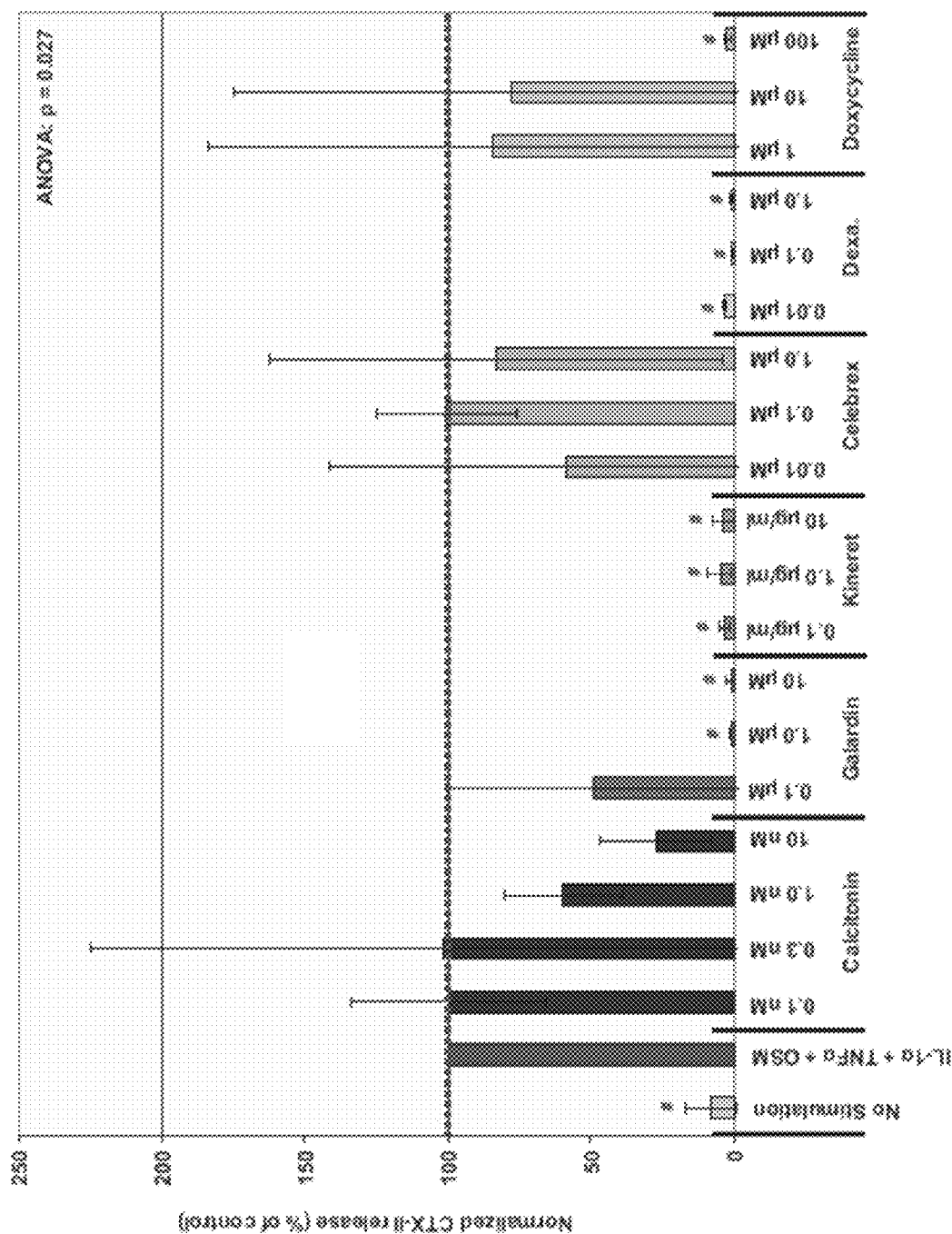
FIG. 2 is a bar chart showing the effect of treatment on collagen release from stimulated bovine articular cartilage explants, measured as CTX-II. The normalized CTX-II release in the culture medium during the three week culture is shown. The dotted line represents the CTX-II release from the control condition to which all conditions are compared.
Figure 3:
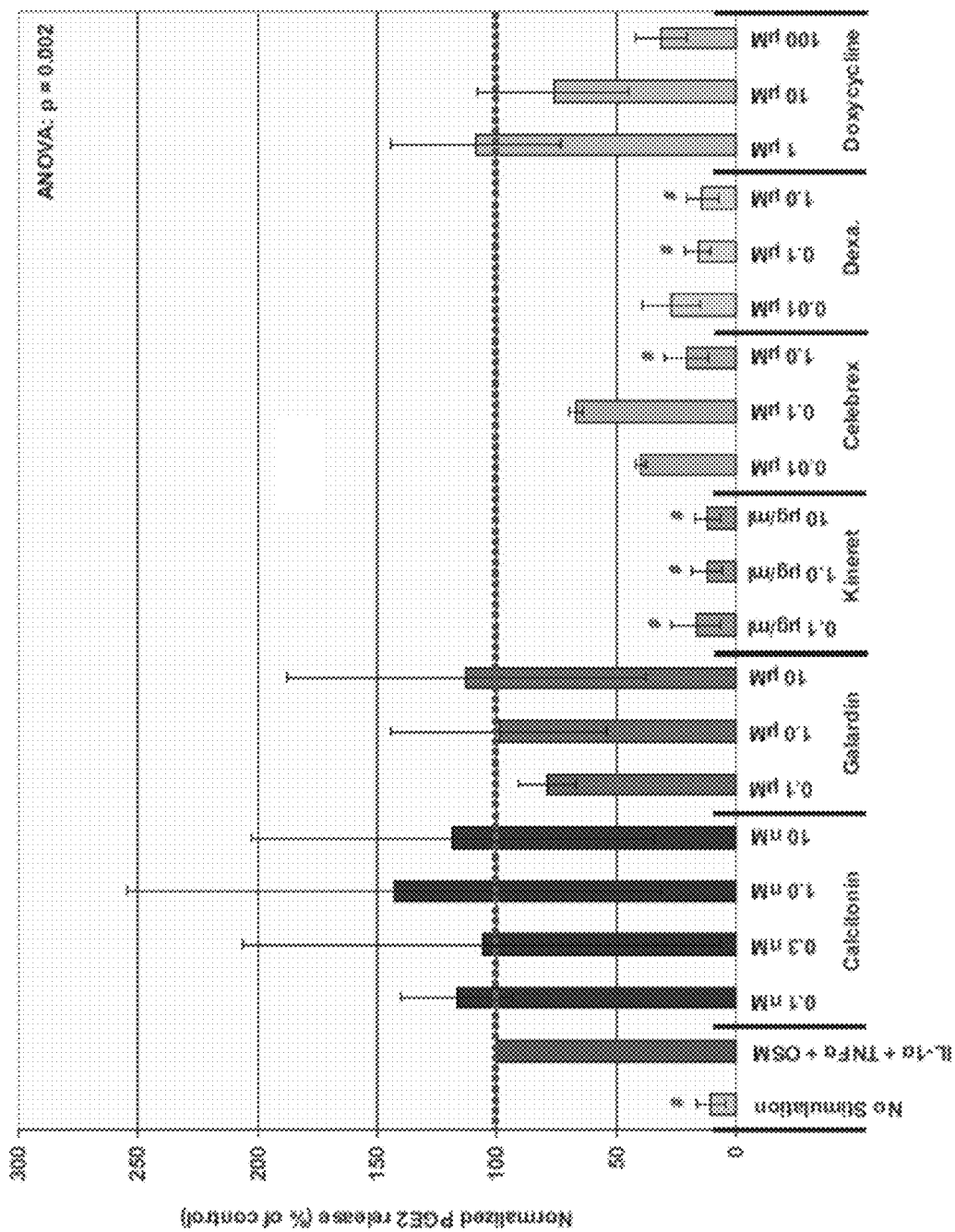
FIG. 3 is a bar chart showing the effect of treatment on PGE2 release from stimulated bovine articular cartilage explants. The normalized PGE2 release in the culture medium during the three week culture is shown. The dotted line represents the PGE2 release from the control condition to which all conditions are compared.

Stimulation of cartilage degradation with cytokine cocktail increased the proteoglycan release from 20 to 92 μg GAG per mg cartilage, see normalized data presented in FIG. 1. Cytokine stimulation increased the collagen release from 12 to 155 ng CTX-II per mg cartilage, see normalized data presented in FIG. 2. Cytokine stimulation increased the PGE2 release from 22 to 199 pg PGE2 per mg cartilage, see normalized data presented in FIG. 3. Each bar represents the mean of three individual paws with the standard deviation. The dotted line represents the value from the control condition to which all conditions are compared. Statistical analysis was performed on the normalized data, differences between groups were tested by ANOVA followed by LSD post-hoc test where # indicates $p<0.05$ and * indicates $p<0.01$.

Galardin inhibited collagen release and slightly inhibited proteoglycan release. Kineret® (anakinra) inhibited all outcome parameters. Celebrex® (celecoxib) inhibited PGE2 release and had a small reducing effect on proteoglycan and collagen release. Dexamethasone inhibited all outcome parameters. Doxycycline inhibited collagen and PGE2 release and had a slight reducing effect on proteoglycan release. The highest ineffective concentration can differ depending on the outcome parameter. Based on the results of phase I, the highest ineffective concentration was determined as illustrated in Table 2. Table 2 provides, for an embodiment of the present disclosure, suggested concentrations for each compound.

TABLE 2

| Compound Name | Proteoglycan release | Collagen Release | PGE2 release | Suggested Concentrations |
|---|---|---|---|---|
| Calcitonin | >10 nM | 0.3-1 nM | >10 nM | 0.5 nM |
| Galardin | 1-10 μM | <0.1 μM | >10 μM | 0.05 μM |
| Kineret ® (anakinra) | <0.1 μg/ml | <0/1 μg/ml | <0.1 μg/ml | 0.01 μM |
| Celebrex ® (celecoxib) | 0.1-1 μM | >10 μM | <0.01 μM | 0.05 μM |
| Dexamethasone | <0.01 μM | <0.01 μM | <0.01 μM | 1 nM |
| Doxycycline | >100 μM | 10-100 μM | 1-10 μM | 10 μM |

Example 2

In this experiment the synergistic effects of Calcitonin in combination with other active agents on cartilage degradation were determined. The results from Example 1 were used to select the concentrations of the compounds for this Example.

Full thickness cartilage was obtained from the metacarpophalangeal joints of approximately 6 months old calves (from a local slaughterhouse). Cartilage punches (4 mm) were taken from the cartilage and placed in culture dishes with culture medium (DMEM+FCS, penicillin, streptomycin and ascorbic acid). Cartilage explants were weighed and explants between about 5 and about 15 mg were divided into a 96-well culture plate with 1 explant per well and 200 μL culture medium. Cartilage degradation was induced by addition of TNFα, IL-1α, and OSM at 10 ng/mL each to the culture medium to induce cartilage degradation. Test agents were then added at different concentrations. During three weeks of culture, the culture medium and the test compounds were refreshed once weekly. In addition fresh calcitonin was added twice weekly to the cartilage explants. Culture medium and cartilage explants were stored at −20° C. until analysis. Each culture condition was cultured in four-fold and the entire experiment was performed on cartilage from three different paws. The different culture conditions are listed below in Table 3.

TABLE 3

| Condition number | 10 ng/ml TNFa 10 ng/ml IL-1a 10 ng/ml OSM | Compound 1 Name | Compound 1 Concentration | Compound 2 Name | Compound 2 Concentration |
|---|---|---|---|---|---|
| 1 | — | — | — | — | — |
| 2 | + | — | — | — | — |
| 3 | + | Calcitonin | 0.5 nM | — | — |
| 4 | + |  | 10 nM | — | — |
| 5 | + | Galardin | 50 nM | — | — |
| 6 | + |  | 10 μM | — | — |
| 7 | + | Celebrex ® | 0.1 μM | — | — |
| 8 | + | (celecoxib) | 1 μM | — | — |
| 9 | + | Dexamethasone | 1 nM | — | — |
| 10 | + |  | 5 μM | — | — |
| 11 | + | Doxycycline | 10 μM | — | — |
| 12 | + |  | 100 μM | — | — |
| 13 | + | BB-94 | 10 nM | — | — |
| 14 | + |  | 100 nM | — | — |
| 15 | + | Calcitonin | 0.5 nM | Galardin | 50 nM |
| 16 | + |  | 10 nM |  | 10 μM |
| 17 | + | Calcitonin | 0.5 nM | Celebrex ® | 0.1 μM |
| 18 | + |  | 0.5 nM | (celecoxib) | 1 μM |
| 19 | + |  | 10 nM |  | 0.1 μM |
| 20 | + |  | 10 nM |  | 1 μM |
| 21 | + | Calcitonin | 10 nM | Dexamethasone | 1 nM |
| 22 | + |  | 10 nM |  | 5 μM |
| 23 | + | Calcitonin | 0.5 nM | Doxycycline | 10 μM |
| 24 | + |  | 10 nM |  | 10 μM |
| 25 | + |  | 10 nM |  | 100 μM |
| 26 | + | Calcitonin | 0.5 nM | BB-94 | 10 nM |
| 27 | + |  | 0.5 nM |  | 100 nM |
| 28 | + |  | 10 nM |  | 10 nM |
| 29 | + |  | 10 nM |  | 100 nM |

Figure 4:
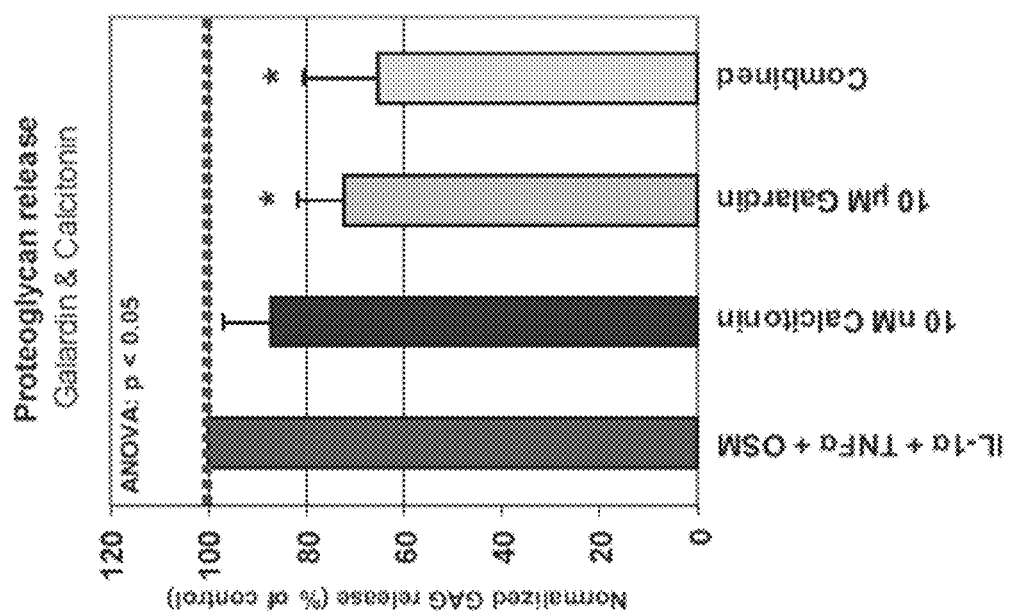
FIG. 4 is a bar chart comparing the effects of Galardin alone, calcitonin alone, and Galardin in combination with calcitonin on proteoglycan release in experiments involving bovine cartilage explants. Normalized data are shown.

FIG. 4 illustrates the effect of Calcitonin and Galardin, individually and in combination, on proteoglycan release. Each bar represents the mean of three individual paws with the standard deviation. Normalized data is shown. Differences between groups were tested by ANOVA followed by LSD post-hoc test where "#" indicates p<0.05 and "*" indicates p<0.01.

As shown in FIG. 4, 10 nM Calcitonin had an effect on the normalized GAG release (reduced the outcome parameter from 100% to 87%), whereas 10 μM of Galardin reduced the outcome parameter significantly (p<0.01) from 100% to 72%. The combination of Calcitonin and Galardin resulted in a significant (p<0.01) reduction to 65%.

Figure 8:
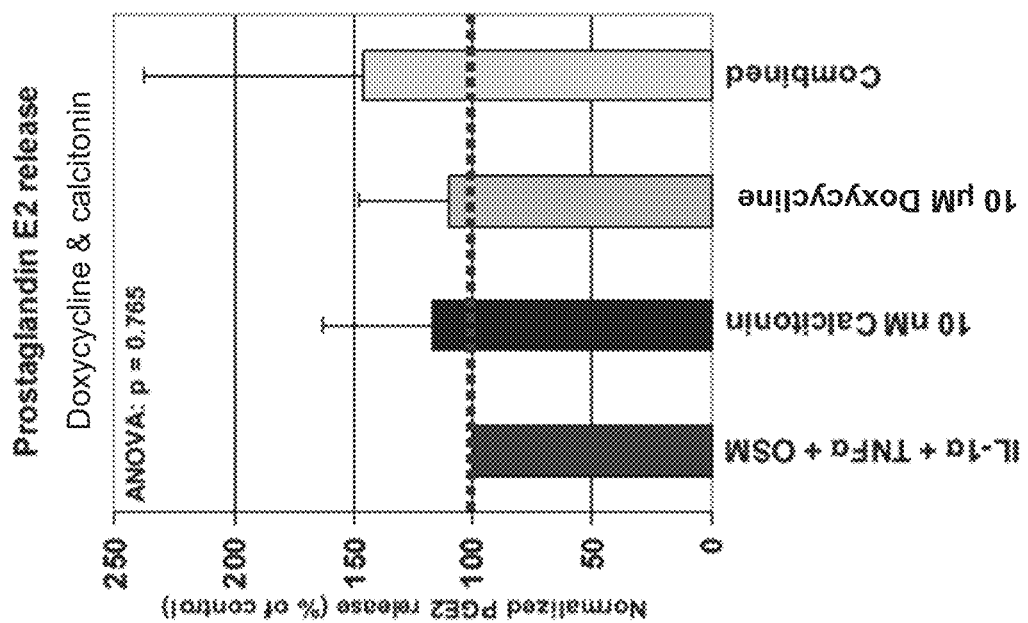
FIG. 8 is a bar chart comparing the effects of Doxycycline alone, calcitonin alone, and Doxycycline in combination with calcitonin on prostaglandin E2 release in experiments involving bovine cartilage explants. Normalized data are shown.

FIGS. 5-8 show the effect of Calcitonin and Doxycycline, individually and in combination, on proteoglycan release (FIG. 5), collagen release (FIG. 6), MMP activity (FIG. 7) and PEG release (FIG. 8). Each bar represents the mean of three individual paws with the standard deviation. For the proteoglycan release the normalized data is shown, while for collagen release and MMP activity the actual values are shown because normalization was not possible. Differences between groups were tested by ANOVA followed by LSD post-hoc test where "#" indicates p<0.05 and "*" indicates p<0.01.

Figure 5:
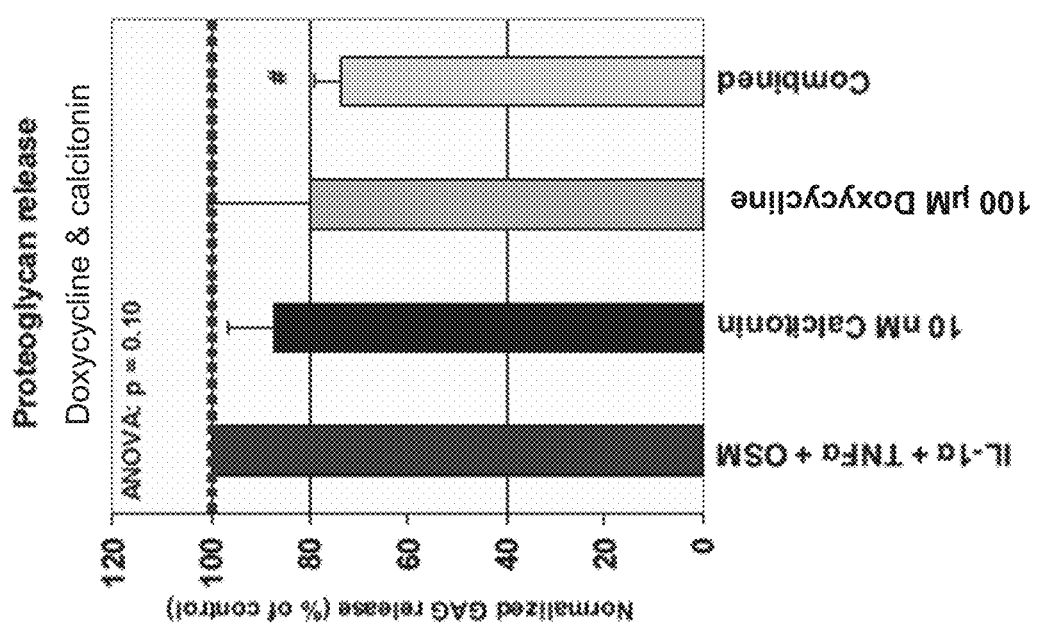
FIG. 5 is a bar chart comparing the effects of Doxycycline alone, calcitonin alone, and Doxycycline in combination with calcitonin on proteoglycan release in experiments involving bovine cartilage explants. Normalized data are shown.

As shown in FIG. 5, 10 nM Calcitonin slightly decreased the GAG release from 100% to 87% and 100 μM Doxycycline decreased the outcome parameter to 80%. The combination of Calcitonin and Doxycycline resulted a further reduction to 73%.

Figure 6:
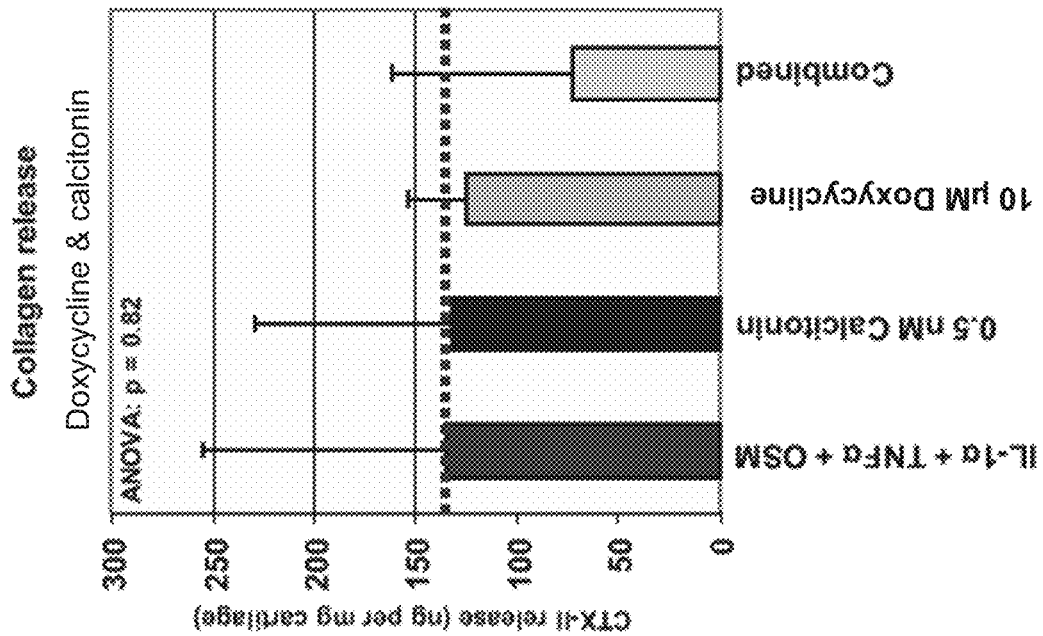
FIG. 6 is a bar chart comparing the effects of Doxycycline alone, calcitonin alone, and Doxycycline in combination with calcitonin on collagen release in experiments involving bovine cartilage explants. Actual values are shown.

As shown in FIG. 6, 0.5 nM Calcitonin slightly decreased the CTX-II release from 135 to 133 ng/mg cartilage and 10 μM Doxycycline decreased the outcome parameter to 125 ng/mg cartilage. The combination of Calcitonin and Doxycycline resulted a further reduction to 73 ng/mg cartilage, suggesting a synergistic effect. This effect is stronger than expected based on the effects of the compounds alone.

Figure 7:
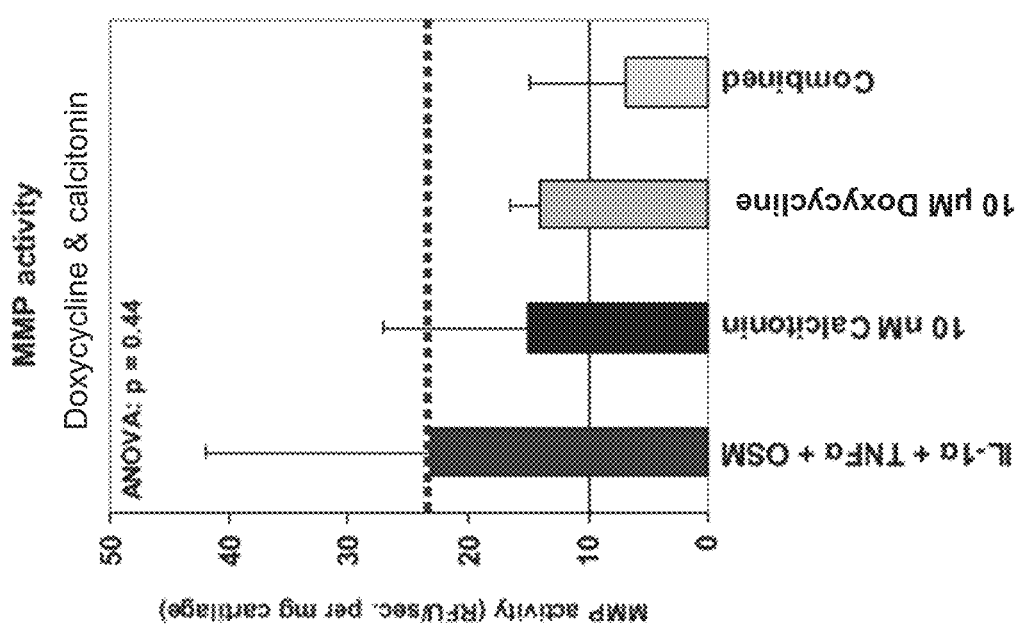
FIG. 7 is a bar chart comparing the effects of Doxycycline alone, calcitonin alone, and Doxycycline in combination with calcitonin on matrix metalloproteinase (MMP) activity in experiments involving bovine cartilage explants. Actual values are shown.

As shown in FIG. 7, 10 nM Calcitonin decreased the MMP activity from 23 to 15 RFU/sec per mg cartilage and 10 μM Doxycycline decreased the outcome parameter to 14 RFU/sec per mg cartilage. The combination of Calcitonin and Doxycycline resulted a further reduction to 7 RFU/sec per mg cartilage.

As shown in FIG. 8, 10 nM Calcitonin increased the PGE2 release from 100 to 117% and 10 μM Doxycycline to 111%. The combination of Calcitonin and Doxycycline resulted a further increase to 145%.

The combination of Calcitonin and Doxycycline seemed to have a larger effect on all outcome parameters than the compounds alone. The strongest effect of this combination was observed on collagen release. The combination of Calcitonin and Doxycycline tended towards a decrease in MMP activity, proteoglycan and collagen release more then Doxycycline alone. The PGE2 release was further increased by the combination of Calcitonin and Doxycycline.

Figure 10:
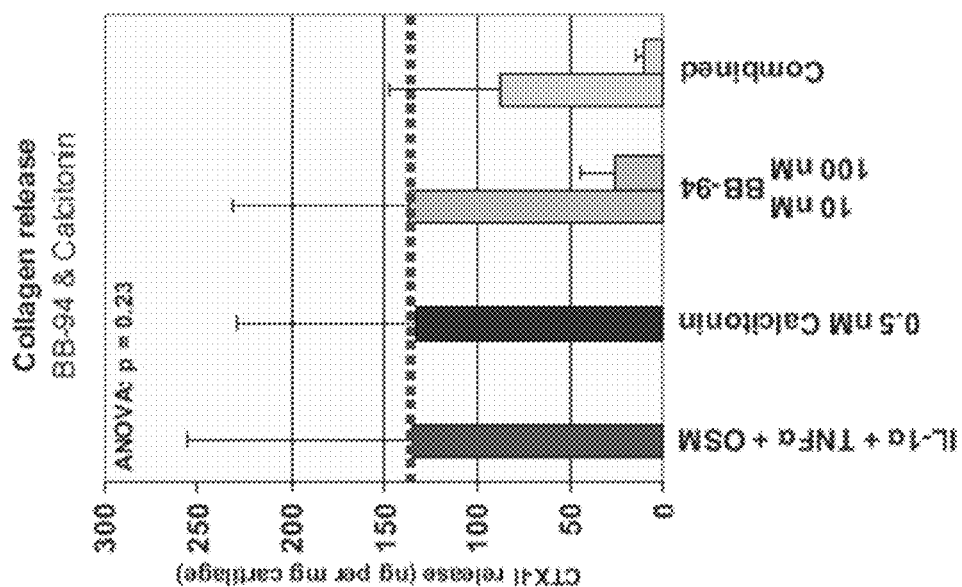
FIG. 10 is a bar chart comparing the effects of BB-94 alone, calcitonin alone, and BB-94 in combination with calcitonin on collagen release in experiments involving bovine cartilage explants. Actual values are shown.
Figure 9:
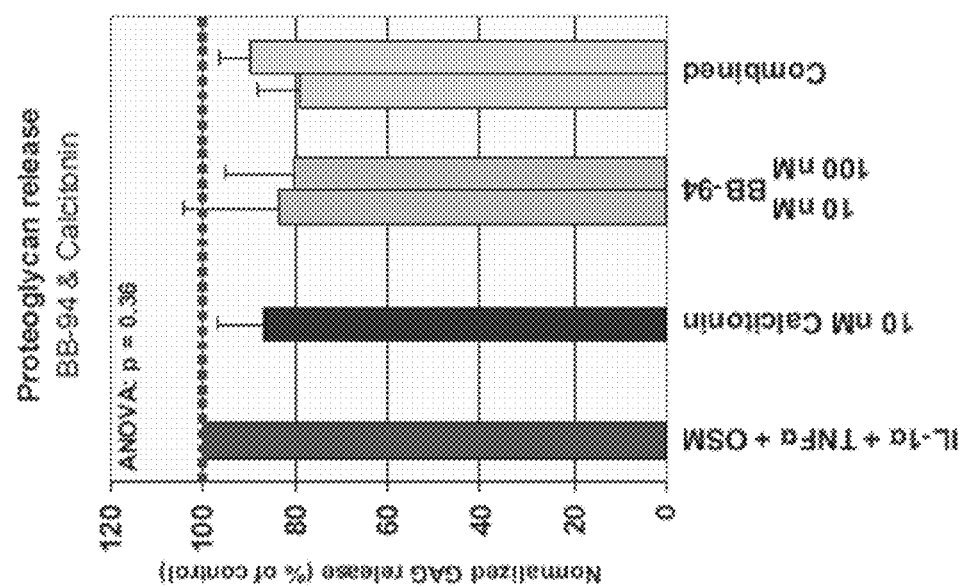
FIG. 9 is a bar chart comparing the effects of BB-94 alone, calcitonin alone, and BB-94 in combination with calcitonin on proteoglycan release in experiments involving bovine cartilage explants. Normalized data are shown. Normalized data are shown.
Figure 11:
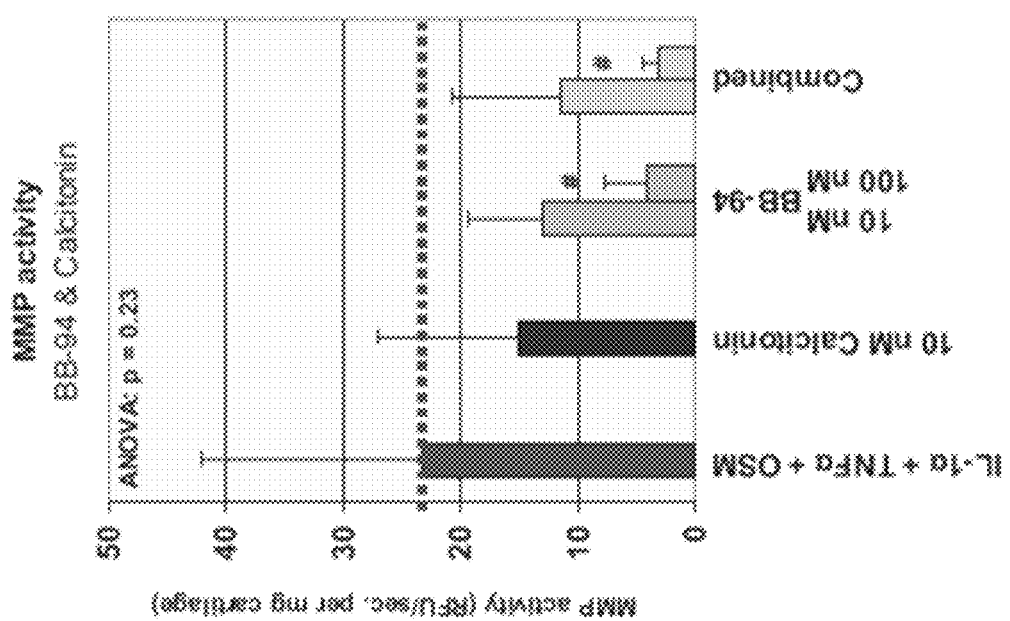
FIG. 11 is a bar chart comparing the effects of BB-94 alone, calcitonin alone, and BB-94 in combination with calcitonin on matrix metalloproteinase (MMP) activity in experiments involving bovine cartilage explants. Actual values are shown.

FIGS. 9-11 show the effect of Calcitonin and BB-94, individually and in combination, on proteoglycan release (FIG. 9), collagen release (FIG. 10) and MMP activity (FIG. 11). Each bar represents the mean of three individual paws with the standard deviation. For the proteoglycan release the normalized data is shown, while for collagen release the actual values are shown because normalization was not possible. Differences between groups were tested by ANOVA followed by LSD post-hoc test where "#" indicates p<0.05 and "*" indicates p<0.01.

As shown in FIG. 9, 10 nM Calcitonin reduced the normalized proteoglycan release from 100 to 87%. BB-94 lowered the proteoglycan release to 83 and 80% at 10 nM and 100 nM respectively. Combining the two compounds resulted in a reduction to 97 and 90% at 10 nM and 100 nM BB-94 respectively.

As shown in FIG. 10, 0.5 nM Calcitonin decreased the CTX-II release from 135 to 133 ng/mg cartilage. BB-94 changed CTX-II release to 137 and 27 ng/mg cartilage at 10 nM and 100 nM respectively. Combining the two compounds resulted in a reduction to 88 and 11 ng/mg cartilage at 10 nM and 100 nM BB-94 respectively. This effect is stronger than expected based on the effects of the compounds alone.

As shown in FIG. 11, 10 nM Calcitonin decreased the MMP activity from 23 to 15 RFU/sec per mg cartilage. BB-94 lowered the MMP activity to 13 and 4 RFU/sec per mg cartilage at 10 nM and 100 nM respectively. Combining the two compounds resulted in a reduction to 11 and 3 RFU/sec per mg cartilage 10 nM and 100 nM BB-94 respectively.

All patents, patent applications, and published references cited herein are hereby incorporated by reference in their entirety. It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method for treating osteoarthritis in a subject in need thereof comprising: administering a therapeutically effective amount of calcitonin, in free or salt form, to the subject; and co-administering, as part of a combination therapy, a therapeutically effective amount of a tetracycline antibiotic, to the subject.

2. The method of claim 1, wherein the calcitonin is selected from the group consisting of human calcitonin, salmon calcitonin, eel calcitonin and elcatonin.

3. The method of claim 1, wherein the calcitonin is salmon calcitonin.

4. The method of claim 3, wherein the subject is a human.

5. The method of claim 1, wherein the calcitonin and the tetracycline antibiotic are each administered to the subject orally.

6. The method of claim 1, wherein the tetracycline antibiotic is doxycycline.

7. The method of claim 6, wherein the subject is a human.

8. The method of claim 1, wherein the calcitonin and the tetracycline antibiotic are administered as a single pharmaceutical composition.

9. The method of claim 1, wherein the calcitonin and the tetracycline antibiotic are administered separately.

10. The method of claim 1, wherein the tetracycline antibiotic is administered at a dosage no higher than 90% of the normal dosage for the tetracycline antibiotic when administered alone for the treatment of osteoarthritis.

11. The method of claim 1, wherein the subject is a human.

12. The method of claim 1, wherein the calcitonin is salmon calcitonin and the tetracycline antibiotic is doxycycline.

13. A method for treating osteoarthritis in a human subject in need thereof comprising: administering a therapeutically effective amount of salmon calcitonin, in free or salt form, to the human subject; and co-administering, as part of a combination therapy, a therapeutically effective amount of doxycycline to the human subject.

* * * * *